(12) United States Patent
Di Napoli

(10) Patent No.: US 6,953,776 B2
(45) Date of Patent: Oct. 11, 2005

(54) OPHTHALMIC FORMULATIONS

(75) Inventor: Guido Di Napoli, Collonge-Bellerive (CH)

(73) Assignee: Laboratoire Medidom S.A., Geneva (CH)

( * ) Notice: Subject to any disclaimer, the term of this patent is extended or adjusted under 35 U.S.C. 154(b) by 0 days.

(21) Appl. No.: 10/721,007

(22) Filed: Nov. 21, 2003

(65) Prior Publication Data

US 2004/0106546 A1 Jun. 3, 2004

Related U.S. Application Data

(62) Division of application No. 09/818,213, filed on Mar. 27, 2001, now Pat. No. 6,677,304.

(30) Foreign Application Priority Data

Apr. 7, 1920 (CH) ..................................... 2000 0694/00

(51) Int. Cl.$^7$ ....................... A61K 38/13; A61K 31/728
(52) U.S. Cl. ........................................... 514/11; 514/54
(58) Field of Search ................................ 514/9–11, 54, 514/2; 435/6, 7.1, 69; 530/317, 321

(56) References Cited

U.S. PATENT DOCUMENTS

| 5,411,952 A | 5/1995 | Kaswan |
|---|---|---|
| 5,474,979 A | 12/1995 | Ding et al. |
| 5,739,105 A | 4/1998 | Kim et al. |
| 5,929,048 A | 7/1999 | Falk et al. |
| 5,951,971 A | 9/1999 | Kawashima et al. |

FOREIGN PATENT DOCUMENTS

| JP | XP-002172972 | 9/1991 |
|---|---|---|
| WO | WO89/01772 | 3/1989 |
| WO | WO93/23010 | 11/1993 |
| WO | WO95/31211 | 11/1995 |

OTHER PUBLICATIONS

Condon, Patrick et al., Double–blind, randomised, placebo controlled, crossover, multicentre study to determine the efficacy . . . , Br. J. of Ophthalmol 1999; 83:1121–1124.

Gowland, G., Fourfold Increase in Efficiency of Cyclosporin A when Combined With Hyaluronan: Evidence for Mode of Drug Transport and Targeting, Int. J. Immunotherapy XIV(1) 1–7 (1998).

Gowland, G. et al., Marked Enhanced Efficacy of Cyclosporin When Combined with Hyaluronic Acid, Clin. Drug. Invest 11(4) 245–250 1996.

*Primary Examiner*—Jon Weber
*Assistant Examiner*—Sheridan Snedden
(74) *Attorney, Agent, or Firm*—Clifford W. Browning; Woodard, Emhardt, Moriarty, McNett & Henry LLP

(57) ABSTRACT

A topical ophthalmic formulation in the form of an aqueous solution comprising a cyclosporin, hyaluronic acid or one of its salts, and polysorbate 80 is described.

9 Claims, No Drawings

OPHTHALMIC FORMULATIONS

CROSS-REFERENCE

This application is a divisional of application Ser. No. 09/818,213, filed Mar. 27, 2001, now U.S. Pat. No. 6,677,304, which claims foreign priority to Switzerland 2000 0694/00 filed Apr. 7, 2000.

BACKGROUND OF THE INVENTION

This invention relates to a topical ophthalmic formulation comprising a cyclosporin.

Cyclosporins represent a class of nonpolar cyclic oligopeptides having numerous pharmacological properties.

They are more particularly known for their immunosuppressive and antiinflammatory activity, and have also been described as being effective in enhancing or reestablishing tear secretion by the lachrymal gland in patients suffering from immune-mediated keratoconjunctivitis sicca.

Cyclosporins of natural origin which in their majority comprise cyclosporin A and in their minority the cyclosporins B to I can be obtained from the fungus *Trichoderma polysporum*.

Like a large number of their analogs and isomers, cyclosporins can also be obtained by synthesis.

The cyclosporin most widely studied and used in pharmacy among the cyclosporins is cyclosporin A.

The activity of a cyclosporin and particularly of cyclosporin A in enhancing or reestablishing tear secretion by the lachrymal gland could be improved by improving absorption of cyclosporin in the lachrymal gland.

For reasons of the very low solubility of cyclosporins in water (20 to 30 μg/mL for cyclosporin A), it has been very difficult to prepare an ophthalmic composition containing a cyclosporin dissolved in an aqueous medium.

It is for this reason that the cyclosporins, known to be lipophilic, have mainly been used in oil-based formulations.

U.S. Pat. No. 4,839,342 describes a topical ophthalmic composition containing a cyclosporin, particularly cyclosporin A, and an excipient, to increase tear production in patients suffering from a lack of tears in the eyes because of a dysfunction of the lachrymal glands. The excipients specifically described are olive oil, peanut oil, castor oil, polyethoxylated castor oil, mineral oils, vaselines, dimethyl sulfoxide, an alcohol, liposomes, silicone oils or their mixtures.

FR-A-2,638,089 describes a topical ophthalmic composition which contains a cyclosporin as the active substance and a vegetable oil such as olive oil, peanut oil, castor oil, sesame oil and maize germ oil as the vehicle, as well as vaseline, to treat illnesses and immunological or inflammatory conditions affecting the eye, and particularly keratoconjunctivitis sicca (KCS) or dry eyes.

However, the oil-based topical ophthalmic formulations have disadvantages such as a disagreeable feeling in the eyes, or lead to dim-sightedness. The oils may moreover reinforce the dry-eye symptoms.

Oil-based topical ophthalmic formulations containing cyclosporin also are physically unstable, because the cyclosporins tend to undergo conformational changes and to precipitate.

These formulations moreover have a poor bioavailability and low eye tolerance, which shows by an irritation of the eyes.

For the purposes of minimizing certain of the above disadvantages such as discomfort in use, and of improving the bioavailability and tolerability of the formulation, it has been proposed in WO 95/31211 to reduce the amount of oil and disperse the oil phase in water so as to form an emulsion, which gave a topical ophthalmic formulation in the form of an emulsion based on water and on oil comprising a cyclosporin mixed with a triglyceride containing long-chain fatty acids such as castor oil and polysorbate 80. This formulation also contains an emulsifier, for instance Pemulen®.

For the purposes of eliminating the problems of cyclosporin precipitation while improving the bioavailability and tolerability of the formulation, an aqueous topical ophthalmic formulation has been proposed in U.S. Pat. No. 5,951,971 which is free of oil and comprises a cyclosporin in a concentration of 0.01 to 0.075% (w/v), water, and a surfactant in an amount of 0.1 to 3% (w/v) intended to improve the solubility of the cyclosporin in water and selected among the polyethoxylated fatty acid esters, the polyethoxylated alkylphenyl ethers, the polyethoxylated alkyl ethers and their mixtures. According to U.S. Pat. No. 5,951,971, it has been found that polysorbate 80, also known as Tween 80, is inappropriate as a surfactant, because it lacks an activity sufficiently high to solubilize a cyclosporin in the desired concentrations in water.

BRIEF SUMMARY OF THE INVENTION

It is the aim of the present invention to eliminate the above disadvantages and particularly the problems of physical stability, and above all to improve the bioavailability of the formulation in the conjunctiva, cornea, and lachrymal gland as well as the eye tolerance of the formulation, by providing a water-based topical ophthalmic formulation containing a cyclosporin.

This aim was achieved when the inventors had found that the presence of hyaluronic acid and of polysorbate 80 in an aqueous ophthalmic formulation containing cyclosporin surprisingly permitted to solubilize the cyclosporin while improving the bioavailability of the formulation in the conjunctiva, cornea, and lachrymal gland and eye tolerance of the formulation when this formulation is administered topically in the eyes.

Hyaluronic acid is a mucopolysaccharide of biological origin widely distributed in nature. It is present in particular in different animal tissues such as the umbilical cords, the synovial fluid, the vitreous body, the cockscombs and various conjunctive tissues such as the skin and the cartilage.

Chemically speaking, hyaluronic acid is a glycosaminoglycan and composed of alternating, repeating groups of D-glucuronic acid and N-acetyl-D-glucosamine forming a linear chain having a molecular weight as high as $13 \times 10^6$ daltons.

The pharmaceutical use of hyaluronic acid or one of its salts, and particularly of sodium hyaluronate, has been widely described in the literature. Since hyaluronic acid or its salts are nonimmunogenic substances and have hydrophilic and viscoelastic properties, they have been used for a number of years as substitute for the eye's vitreous fluid or as a supporting medium in eye surgery, as described for example in U.S. Pat. No. 4,141,973.

Other applications of hyaluronic acid in ophthalmology have also been described.

Thus, EP-A-0,698,388 describes an aqueous ophthalmic composition comprising a salt of hyaluronic acid at a concentration of 0.05 to 2% as an agent increasing the viscosity, to be used as artificial tears.

WO-A-89/017772 describes an oil-based topical ophthalmic composition containing a cyclosporin, intended to enhance or reestablish tear secretion by the lachrymal gland. Hyaluronic acid is cited in a list of products that can be incorporated into the formulation as additives or additional active agents.

According to a first aspect, the subject of the present invention is a water-based topical ophthalmic formulation comprising a cyclosporin, hyaluronic acid or one of its salts, and polysorbate 80.

According to a second aspect, the subject of the present invention is the use of a cyclosporin in association with hyaluronic acid or one of its salts and with polysorbate 80 in preparing a water-based formulation intended for a topical ophthalmic utilization.

The present invention thus provides an ophthalmic formulation in the form of an aqueous solution in which the cyclosporin is solubilized in a micellar form, a formulation which is stable and has a good bioavailability in the conjunctiva, the cornea, the lachrymal gland and the aqueous humor as well as an eye tolerance considerably improved over those in a formulation where the cyclosporin is solubilized in a water-oil emulsion.

Other advantages of the present invention will become apparent from the following detailed description of the invention.

DETAILED DESCRIPTION OF THE INVENTION

In the present application, the term "cyclosporin" is to be understood to include whatever individual member of the class of cyclosporins and their mixtures, unless a particular cyclosporin is specified.

It must also be noted that in the present application, the term "hyaluronic acid" indifferently means the hyaluronic acid in its acid form or in the form of one of its salts.

In conformity with the present invention, the formulation of the present invention contains a cyclosporin, hyaluronic acid or one of its salts, and polysorbate 80.

The formulation according to the present invention preferably comprises 0.02 to 2% by weight of cyclosporin, 0.01 to 2% by weight of hyaluronic acid or one of its salts, and 0.5 to 40% by weight of polysorbate 80, based on the formulation's total weight.

The cyclosporins that may be contained in the formulation of the present invention can be of natural or synthetic origin.

According to a preferred embodiment, the cyclosporin contained in the formulation is a cyclosporin A.

One cyclosporin A that can be used to prepare the formulation of the present invention is for instance a commercial cyclosporin A furnished by SIGMA in Switzerland.

The hyaluronic acid contained in the formulation can be, either in its acid form or in the form of one of its salts such as an alkali metal or alkaline-earth metal hyaluronate, for instance sodium hyaluronate, potassium hyaluronate, magnesium hyaluronate, calcium hyaluronate or others.

The hyaluronic acid or its salt preferably have a weight-average molecular weight that is not below 1,000,000 daltons, more preferably a weight-average molecular weight in the region of 1,300,000 to 3,000,000 daltons. The molecular weight is preferably about 1,700,000 daltons.

Preferably the hyaluronic acid is in the form of sodium hyaluronate.

Polysorbate 80, also known as Tween 80, is a polyethoxylated sorbitan monooleate known for its uses as a surfactant.

A polysorbate 80 that can be used to prepare the formulation of the present invention is for instance a commercial polysorbate 80 furnished for instance by SIGMA.

In a particularly preferred embodiment, the composition comprises 0.2% by weight of cyclosporin A, 0.1% by weight of hyaluronic acid and 5% by weight of polysorbate 80, based on the formulation's total weight.

The formulation of the present invention can moreover contain additives such as sorbitol, which is used as an isosmotic agent. Sorbitol has the advantage of having a hydrodynamic volume larger than that of NaCl for instance. Other possible additives are mannitol, polyalcohols and the chlorides of sodium and potassium.

For the formulation of the present invention to be physiologically acceptable, it should preferably have a pH in the range from 6.5 to 7.5 and an osmolality in the range from 290 to 310 mosm/L, preferably 300 mosm/L.

The formulation of the present invention can be packaged as single doses.

The topical formulation of the present invention is administered into the eye in the form of drops, and is useful for enhancing or reestablishing the secretion of tears by the lachrymal gland, and also for stimulating or reestablishing the activity of the lachrymal gland, particularly in patients suffering from keratoconjunctivitis sicca, dry-eye syndrome, Sjögren syndrome, chronic vernal keratoconjunctivitis, and as postoperative prophylactic in keratoplasty.

The following examples are intended to illustrate the present invention and its advantages. They must in no case be considered as limiting the scope of the present invention.

EXAMPLES

Examples of formulations in conformity with the present invention are presented in Table 1 below.

The formulation Ref. 1 is a reference formulation not containing cyclosporin.

TABLE 1

| | Formulation | | | | | |
|---|---|---|---|---|---|---|
| Constituents | 1 | 2 | 3 | 4 | 5 | Ref. 1 |
| Cyclosporin A (%) | 0.02 | 0.10 | 0.20 | 0.50 | 2.00 | — |
| Sodium hyaluronate (%) | 0.05 | 0.10 | 0.10 | 0.10 | 0.20 | 0.10 |
| Tween 80 (%) | 0.05 | 2.50 | 5.00 | 10.00 | 20.00 | 5.00 |
| $Na_2HPO_4 \cdot 12H_2O$ (%) | 0.08 | 0.08 | 0.08 | 0.10 | 0.15 | 0.08 |
| Sorbitol (%) | 5.46 | 5.35 | 5.16 | 4.70 | 3.76 | 5.25 |
| Purified water added to | 100 mL | 100 mL | 100 mL | 100 mL | 100 mL | 100 mL |
| pH | 7.0–7.4 | 7.0–7.4 | 7.0–7.4 | 7.0–7.4 | 7.3–7.4 | 7.0–7.4 |
| mosm/L | 295–305 | 295–305 | 295–305 | 295–305 | 295–305 | 295–305 |

The formulations 1 to 5 and Ref. 1 have been subjected to tests in order to evaluate their eye tolerance, and formulations 1 to 5 have been subjected to a stability test.

Eye Tolerance of Formulations 1 to 5 and Ref. 1

The evaluation of local tolerability of the formulations 1 to 5 and Ref. 1 has been performed with albino rabbits from New Zealand (six for each group, three males and three females), to whom 12 instillations of 0.1 mL each of the formulation to be tested have been administered in 30-minute intervals into the right conjunctival arcade.

The condition of the eye tissues was evaluated in conformity with the Draize test (S. C. Gad and C. P. Chengelis, "Ocular Irritation Test", in Acute Toxicology Testing, Telford Press, Caldewell N.J. USA, pp. 51–80). The test was performed 30 min after the last instillation. The readings were taken by two observers totally ignorant about the treatment who attributed arbitrary points for the condition of the conjunctiva (palpebral and bulbar), the cornea and the iris.

The treated eye also was subjected to a test with fluorescein according to the following procedure. Forty minutes after the last instillation of the formulation being tested, and after the Draize test, a solution containing 2% of fluorescein in physiological saline was instilled into the eye to be treated, and the excess of fluorescein eliminated by washing the eye with sterile physiological saline. The eye tissues are then carefully observed in order to evaluate the quantity of fluorescein that had been absorbed. With this evaluation, for which a slit lamp was used, it could be shown that all formulations had good tolerability, that is, the formulations 1 to 5 containing cyclosporin A and the formulation Ref. 1 not containing cyclosporin A.

In the Draize test the cornea and the iris always exhibited a normal aspect. The conjunctiva was found to be normal without edema or secretion, except that in each of the three groups of rabbits treated with formulations 3, 4, and 5 containing 0.20, 0.5 and 2% cyclosporin A, respectively, two out of six treated eyes exhibited a hyperemia of the vessels in the central region, which according to the evaluation test corresponds to an even better tolerability.

In the fluorescein test, there was no difference between the different formulations; none of the eyes treated had absorbed the fluorescein.

Stability of Formulations 1 to 5 of the Present Invention

All formulations were found to be stable at ambient temperature, and a precipitation of cyclosporin A occurred in none of the formulations 1 to 5 within the 12 months following preparation of the formulation.

Formulation 3 of the present invention has subsequently be compared with an oil-water type emulsion with respect to the bioavailability of cyclosporin A in the eye tissues and to eye tolerability.

Comparison Between Formulation 3 of the Present Invention and an Oil-Water Type Emulsion Formulation 3 of the present invention was compared with an oil-water emulsion called CYCLOIL, which is a formulation according to patent application WO-A-95/31211, with respect to eye tolerability and the bioavailability of cyclosporin A in the eye tissues.

The compositions of these two formulations are summarized in the following Table 2.

TABLE 2

| Constituents | Formulation 3 | CYCLOIL |
|---|---|---|
| Cyclosporin A (%) | 0.20 | 0.20 |
| Sodium hyaluronate (%) | 0.10 | — |
| Castor oil (%) | — | 1.25 |
| Tween 80 (%) | 5.00 | 1.00 |
| Glycerol (%) | — | 2.00 |
| Pemulen® TR-2 (%) | — | 0.05 |
| $Na_2HPO_4 \cdot 12H_2O$ (%) | 0.08 | — |
| Sorbitol (%) | 5.16 | — |
| Purified water added to | 100 mL | 100 mL |
| pH | 7.0–7.4 | 7.0–7.4 |
| mosm/L | 295–305 | 290–310 |

Ocular Bioavailability

In this experiment the concentrations of cyclosporin A were determined in the conjunctiva, the cornea, the aqueous humor and the lachrymal gland after topical administration of the two formulations, viz., Formulation 3 of the present invention and CYCLOIL.

The tests were performed with male albino rabbits from New Zealand. The rabbits were divided into two groups of 15 rabbits and treated in both eyes with 50 µL per eye, with the two formulations to be tested. Conjunctiva, cornea, aqueous humor and lachrymal gland were sampled 1, 3, 6, 12, and 24 hours after instillation, each time from three rabbits of the two groups, after sacrificing the animals. The eyes were enucleated and washed with physiological saline before taking aqueous humor (about 400 µL), cornea (about 120 mg), conjunctiva (about 120 mg), and lachrymal gland (about 800 mg).

The quantitative determination of cyclosporin A was realized by inverse-phase HPLC with isocratic elution and UV-spectroscopic detection. The chromatograph was a Varian instrument, the chromatographic conditions were as follows:

column: C18.60×4.6 mm, 3 µm (Alltech)

mobile phase: acetonitrile/isopropanol/$H_2O$ (66/2/32)

flow velocity: 0.7 mL/min column temperature: 72° C.

detection: UV 205 nm (0.1–0.002 AUFS)

injection volume: 25–50 µL retention time: 9.1 min

The samples to be chromatographed were prepared as follows:

Aqueous Humor

To 300 µL of the aqueous humor 150 µL of acetonitrile were added and the solution thus obtained was vortex-agitated for about 1 min, then it was centrifuged during 3 min at 3000 g. The supernatent was transferred to a bottle, treated with 15 mg $ZnSO_4$ and 15 mg $CdSO_4$, vortex-agitated during 1 min, and centrifuged during 2 in at 2000 g. The organic phase was filtered through 0.45 µm, and 50 to 75 µL were injected into the column.

Cornea, Conjunctiva and Lachrymal Gland

The tissues were exactly weighed, homogeneized in the cold with methanol (about 1.0 mL), centrifuged at 3000 g during 15 min, the supernatent was taken up with methanol (about 1 mL) and dried under vacuum at about 40° C., the residue was taken up with acetonitrile (150 µL), treated with anhydrous $(NH_4)_2SO_4$, vortex-agitated for 1 min, and centrifuged during 2 min at 2000 g. The organic phase was filtered through 0.45 µm, and 50 to 75 µL were injected into the column.

Analytical Method

The concentrations of cyclosporin A in the conjunctiva, cornea, lachrymal gland and aqueous humor of the rabbits are presented in Tables 3 to 6.

Concentrations of Cyclosporin A in the Conjunctiva

Table 3 below shows the concentrations (ng/g) of cyclosporin A in the conjunctiva of rabbits treated with Formulation 3 of the present invention and with CYCLOIL, 1, 3, 6, 12, and 24 hours after instillation of 50 µL into the conjunctival sac of both eyes.

TABLE 3

|  | Formulation 3 (invention) | CYCLOIL (comparison) |
|---|---|---|
| concentration 1 h after instillation (ng/g) | 1170 ± 170 | 820 ± 155 |
| concentration 3 hours after instillation (ng/g) | 900 ± 215 | 713 ± 187 |
| concentration 6 hours after instillation (ng/g) | 616 ± 102 | 370 ± 78 |
| concentration 12 hours after instillation (ng/g) | 502 ± 95 | 250 ± 70 |
| concentration 24 hours after instillation (ng/g) | 198 ± 40 | 75 ± 25 |
| $AUC_{0-24}$ (ng $g^{-1}$ $h^{-1}$) | 12483 ± 234 | 7378 ± 1891 |
| $C_{max}$ (ng/g) | 1170 ± 170 | 820 ± 155 |
| $T_{max}$ (hours) | 1 | 1 |

One can see from Table 3 above that Formulation 3 of the present invention guarantees a better bioavailability of cyclosporin in the conjunctiva at all points in time where samples were taken, as compared to the formulation CYCLOIL.

The maximum concentration is found after the first hour, although one may suppose that the highest absolute cyclosporin concentrations in the conjunctiva would be found just after instillation.

The water-based Formulation 3 of the present invention guarantees cyclosporin A concentrations which in all samples are always higher than those with the water-oil emulsion CYCLOIL.

The AUC (areas under the curve) are 12483±234 ng $g^{-1}$ $h^{-1}$ for Formulation 3 of the present invention, and 7378±1891 ng $g^{-1}$ $h^{-1}$ for the oil-water emulsion CYCLOIL.

The same results are obtained in the cornea.

Cyclosporin A Concentrations in the Cornea

Table 4 shows cyclosporin A concentrations (ng/g) in the cornea of rabbits treated with Formulation 3 of the present invention and with oil-based CYCLOIL, 1, 3, 6, 12, and 24 hours after instillation of 50 µL into the conjunctival sac of both eyes.

TABLE 4

|  | Formulation 3 (invention) | CYCLOIL (comparison) |
|---|---|---|
| concentration 1 hour after instillation (ng/g) | 2995 ± 750 | 2070 ± 1115 |
| concentration 3 hours after instillation (ng/g) | 3350 ± 920 | 1991 ± 630 |
| concentration 6 hours after instillation (ng/g) | 2520 ± 870 | 2420 ± 870 |
| concentration 12 hours after instillation (ng/g) | 2228 ± 490 | 1825 ± 690 |
| concentration 24 hours after instillation (ng/g) | 1590 ± 220 | 450 ± 190 |
| $AUC_{0-24}$ (ng $g^{-1}$ $h^{-1}$) | 53800 ± 13070 | 38097 ± 1397 |
| $C_{max}$ (ng/g) | 3350 ± 920 | 2420 ± 870 |
| $T_{max}$ (hours) | 3 | 6 |

It can be seen from Table 4 above that the maximum concentration of the medicine is obtained after the third hour with Formulation 3 of the present invention (3350±920 ng/g), and after the sixth hour with CYCLOIL (2420±870 ng/g).

The water-based Formulation 3 of the present invention guarantees cyclosporin A concentrations which in all samples are always higher than those with the oil-water emulsion CYCLOIL.

Cyclosporin A Concentrations in the Lachrymal Gland

Table 5 shows the cyclosporin A concentrations (ng/g) in the lachrymal gland of rabbits treated with Formulation 3 of the present invention and with oil-based CYCLOIL, 1, 3, 6, 12, and 24 hours after instillation of 50 µL into the conjunctival sac of both eyes.

TABLE 5

|  | Formulation 3 (invention) | CYCLOIL (comparison) |
|---|---|---|
| concentration 1 hour after instillation (ng/g) | 88 ± 29 | 22 ± 10 |
| concentration 3 hours after instillation (ng/g) | 149 ± 45 | 42 ± 16 |
| concentration 6 hours after instillation (ng/g) | 135 ± 33 | 53 ± 18 |
| concentration 12 hours after instillation (ng/g) | 54 ± 22 | 21 ± 10 |
| concentration 24 hours after instillation (ng/g) | 38 ± 19 | 17 ± 10 |
| $AUC_{0-24}$ (ng $g^{-1}$ $h^{-1}$) | 1826 ± 616 | 668 ± 286 |
| $C_{max}$ (ng/g) | 149 ± 45 | 53 ± 18 |
| $T_{max}$ (hours) | 3 | 6 |

The water-based Formulation 3 of the present invention shows a maximum concentration of cyclosporin A after the third hour (149±45 ng/g), while CYCLOIL shows a maximum concentration of the cyclosporin of 53±16 ng/g after the sixth hour.

As expected, the cyclosporin A concentrations in the lachrymal gland which are reported in Table 5 are distinctly lower than those obtained in the conjunctiva and cornea, but still always exceed the limits of sensitivity of the method (15 ng/g).

It can be seen above that the bioavailability of Formulation 3 of the present invention is much higher than that of CYCLOIL, and the cyclosporin A moreover is still present 24 hours after instillation, certainly at lower concentrations, but still measurable. The ratio $AUC_{AN-023}/AUC_{cycloil}$, which represents the ratio of bioavailabilities, has a value of about three.

Cyclosporin A Concentrations in the Aqueous Humor

Table 6 shows the cyclosporin A concentrations (ng/g) in the aqueous humor of rabbits treated with Formulation 3 of the present invention and with oil-based CYCLOIL, 1, 3, 6, 12, and 24 hours after instillation of 50 µL into the conjunctival sac of both eyes.

TABLE 6

|  | Formulation 3 (invention) | CYCLOIL (comparison) |
|---|---|---|
| concentration 1 hour after instillation (ng/g) | 40 ± 12 | 12 ± 13 |
| concentration 3 hours after instillation (ng/g) | 41 ± 14 | 18 ± 7 |
| concentration 6 hours after instillation (ng/g) | 31 ± 8 | 22 ± 11 |
| concentration 12 hours after instillation (ng/g) | 27 ± 9 | 16 ± 4 |

TABLE 6-continued

|  | Formulation 3 (invention) | CYCLOIL (comparison) |
|---|---|---|
| concentration 24 hours after instillation (ng/g) | 16 ± 5 | 14 ± 2 |
| $AUC_{0-24}$ (ng $g^{-1}$ $h^{-1}$) | 641 ± 14 | 390 ± 119 |
| $C_{max}$ (ng/g) | 41 ± 14 | 22 ± 11 |
| $T_{max}$ (hours) | 3 | 6 |

The maximum concentration of cyclosporin instilled as an aqueous formulation (Formulation 3 of the present invention) was revealed after the third hour (44±14 ng/mL), while for the oil-based emulsion CYCLOIL the maximum was revealed after the sixth hour (22±11 ng/mL).

The cyclosporin A concentrations in the aqueous humor of rabbits treated by instillation of 50 μL with both of the formulations tested proved to be relatively low as compared to the two tissues which constitute the surface of the eye (cornea and conjunctiva). Yet for the aqueous humor, like for the other eye tissues, the bioavailability of the cyclosporin administered as an aqueous formulation was higher than that instilled as water-oil emulsion.

Evaluation of Tolerability

The tolerability of Formulation 3 of the present invention and of CYCLOIL has been evaluated in conformity with a Draize test modified as described previously.

Two groups of six animals, each comprising three male and three female albino rabbits from New Zealand, have been treated in the eye by performing 12 instillations of 0.1 mL of the two formulations to be tested, during six hours with 30 minute intervals.

The Draize test for evaluation of the tolerability has been realized 30 min after the last instillation. After this test, 40 min after the last instillation, the fluorescein test was performed. The results of these two tests are reported in Tables 7 and 8.

In the following Table 7, the degrees of reddening of the conjunctiva of rabbits treated with Formulation 3 of the present invention and with CYCLOIL by instillation into the right eye are reported in conformity with the Draize test. The reddening has been evaluated according to an arbitrary scale. The treatment was performed 12 times with 30-minute intervals. The evaluation occurred 30 min after the last instillation.

TABLE 7

| Rabbit No. | Sex | Formulation | Degree of reddening of the conjunctiva |
|---|---|---|---|
| 1 | M | 3 | 0 |
| 2 | M | 3 | 1 |
| 3 | M | 3 | 1 |
| 4 | F | 3 | 0 |
| 5 | F | 3 | 0 |
| 6 | F | 3 | 0 |
| Average |  |  | 0.33 ± 0.52 |
| Frequency |  |  | 2/6 |
| 7 | M | CYCLOIL | 1 |
| 8 | M | CYCLOIL | 1 |
| 9 | M | CYCLOIL | 2 |
| 10 | F | CYCLOIL | 1 |
| 11 | F | CYCLOIL | 1 |
| 12 | F | CYCLOIL | 0 |
| Average |  |  | 1.00 ± 0.63 |
| Frequency |  |  | 5/6 |

It can be seen that Formulation 3 of the present invention has given a reddening in only two of six cases, with a certain hyperemia in the central region, while the oil-based CYCLOIL showed a frequency of five out of six rabbits. With CYCLOIL the degree of reddening was weak for four rabbits, but one hour after the last instillation, one rabbit exhibited a diffuse hyperemia of crimson red color where the individual vessels were hard to distinguish.

None of the rabbits exhibited an edema or higher than normal secretion of the conjunctiva.

The following Table 8 reports the degrees of hyperemia of the iris of rabbits treated with Formulation 3 of the present invention and with CYCLOIL by instillation into the right eye. The iris hyperemia was evaluated with the aid of an arbitrary scale. The treatment was administered 12 times with 30-minute intervals. The evaluation occurred 30 min after the last instillation.

TABLE 8

| Rabbit No. | Sex | Formulation | Degree of iris hyperemia |
|---|---|---|---|
| 1 | M | 3 | 0 |
| 2 | M | 3 | 0 |
| 3 | M | 3 | 1 |
| 4 | F | 3 | 0 |
| 5 | F | 3 | 0 |
| 6 | F | 3 | 0 |
| Average |  |  | 0.17 ± 0.41 |
| Frequency |  |  | 1/6 |
| 7 | M | CYCLOIL | 0 |
| 8 | M | CYCLOIL | 1 |
| 9 | M | CYCLOIL | 1 |
| 10 | F | CYCLOIL | 0 |
| 11 | F | CYCLOIL | 1 |
| 12 | F | CYCLOIL | 0 |
| Average |  |  | 0.50 ± 0.55 |
| Frequency |  |  | 3/6 |

Only one rabbit of the group treated with Formulation 3 of the present invention showed a very slight hyperemia at the secondary iris vessels and not at the tertiary vessels.

The frequency of this very light type of hyperemia has been three out of six in the group treated with CYCLOIL.

Table 9 below reports the degrees of opacity of the cornea of rabbits treated with Formulation 3 according to the invention and with CYCLOIL, instilled into the right eye. The opacity was evaluated according to an arbitrary scale. The treatment was administered 12 times with 30-minute intervals. The evaluation occurred 30 min after the last instillation.

TABLE 9

| Rabbit No. | Sex | Formulation | Degree of opacity of the cornea |
|---|---|---|---|
| 1 | M | 3 | 0 |
| 2 | M | 3 | 0 |
| 3 | M | 3 | 0 |
| 4 | F | 3 | 0 |
| 5 | F | 3 | 0 |
| 6 | F | 3 | 0 |
| Average |  |  | 0 |
| Frequency |  |  | 0/6 |
| 7 | M | CYCLOIL | 0 |
| 8 | M | CYCLOIL | 0 |
| 9 | M | CYCLOIL | 1 |
| 10 | F | CYCLOIL | 0 |
| 11 | F | CYCLOIL | 0 |
| 12 | F | CYCLOIL | 0 |
| Average |  |  | 0.17 ± 0.41 |
| Frequency |  |  | 1/6 |

Only one rabbit of the group treated with CYCLOIL showed a region of dispersed opacity of the cornea, which was however such as to still have good visibility of the iris.

Table 10 below reports the degree of fluorescein absorption in the corneal epithelium of rabbits treated with Formulation 3 according to the invention and with CYCLOIL instilled into the right eye. The absorption was evaluated on an arbitrary scale. The treatment was administered 12 times with 30-minute intervals. The evaluation occurred 40 min after the last instillation.

TABLE 10

| Rabbit No. | Sex | Formulation | Degree of fluorescein absorption |
|---|---|---|---|
| 1 | M | 3 | 0 |
| 2 | M | 3 | 1 |
| 3 | M | 3 | 0 |
| 4 | F | 3 | 0 |
| 5 | F | 3 | 1 |
| 6 | F | 3 | 0 |
| | Average | | 0.33 ± 0.52 |
| | Frequency | | 2/6 |
| 7 | M | CYCLOIL | 0 |
| 8 | M | CYCLOIL | 1 |
| 9 | M | CYCLOIL | 2 |
| 10 | F | CYCLOIL | 1 |
| 11 | F | CYCLOIL | 0 |
| 12 | F | CYCLOIL | 0 |
| | Average | | 0.67 ± 0.82 |
| | Frequency | | 3/6 |

It can be seen above that Formulation 3 of the present invention is also better tolerated in the fluorescein test. Actually three corneas of the group treated with CYCLOIL had absorbed fluorescein, one of which, the rabbit No. 9, exhibited accentuated fluorescent spots, even though the structures of the various tissues could still be distinguished, albeit with a loss of detail, if proper illumination was used.

Only two of the six rabbits treated with Formulation 3 of the present invention exhibited rare, small fluorescent spots, but no coloration was visible around the outer edge of the pupil.

The above results thus clearly demonstrate that the aqueous formulation according to the present invention proves, not only better tolerated but also more highly bioavailable than an oil-water emulsion on the basis of castor oil, Tween 80 (polysorbate 80), glycerol, and Pemulen® TR-2 (CYCLOIL).

What is claimed is:

1. A method for preparing an aqueous formulation for topical ophthalmic use comprising the step of associating a cyclosporin with hyaluronic acid or one of its salts and polysorbate 80.

2. The method for preparing an aqueous formulation according to claim 1, wherein the formulation comprises 0.02 to 2% by weight of cyclosporin, 0.01 to 2% by weight of hyaluronic acid or one of its salts, and 0.5 to 40% by weight of polysorbate 80, based on the formulation's total weight.

3. The method for preparing an aqueous formulation according to claim 1, wherein the cyclosporin is a cyclosporin A.

4. The method for preparing an aqueous formulation according to claim 1, wherein the hyaluronic acid or its salt has a weight-average molecular weight not inferior to 1,300,000 daltons.

5. The method for preparing an aqueous formulation according to claim 4, wherein the hyaluronic acid or its salt has a weight-average molecular weight situated in the region from 1,300,000 to 3,000,000 daltons.

6. The method for preparing an aqueous formulation according to claim 1, wherein the hyaluronic acid is present as alkali metal or alkaline-earth metal hyaluronate.

7. The method for preparing an aqueous formulation according to claim 6, wherein the hyaluronic acid is present as sodium hyaluronate.

8. A method for treating conditions selected from the group consisting of keratoconjunctivitis sicca (KCS), Sjögren's syndrome, dry-eye syndrome and chronic vernal keratoconjunctivitis comprising the step of administering a formulation of a cyclosporin, hyaluronic acid or one of its salts, and polysorbate 80.

9. A method for post-operative prophylactic treatment in keratoplasty comprising the step of using a formulation comprising a cyclosporin, hyaluronic acid or one of its salts, and polysorbate 80.

* * * * *